United States Patent [19]
Driessen et al.

[11] Patent Number: 5,312,909
[45] Date of Patent: May 17, 1994

[54] RECOMBINANT DNA ENCODING NEUTRAL TREHALASE

[75] Inventors: Marianne Driessen, Zoeterwoude Rijndijk; Klaas A. Osinga, Voorschoten; Margareta A. Herweijer, Amsterdam, all of Netherlands

[73] Assignee: Gist Brocades, N.V., Delft, Netherlands

[21] Appl. No.: 673,833

[22] Filed: Mar. 22, 1991

Related U.S. Application Data

[63] Continuation-in-part of Ser. No. 577,888, Sep. 5, 1990, abandoned.

[30] Foreign Application Priority Data

Mar. 28, 1990 [EP] European Pat. Off. ............ 90200757
Dec. 20, 1990 [EP] European Pat. Off. ............ 90203462

[51] Int. Cl.$^5$ ..................... C12N 15/56; C12N 15/31
[52] U.S. Cl. .................. 536/23.2; 435/161; 435/200; 435/254.21; 435/320.1; 435/942
[58] Field of Search .............. 435/69.1, 100, 172.1, 435/172.3, 194, 195, 252.3, 320.1; 935/37, 55, 69; 536/23.2

[56] References Cited

FOREIGN PATENT DOCUMENTS 0306107 3/1989 European Pat. Off. ..... C12N 15/00

OTHER PUBLICATIONS

Oda et al. "Selection of Yeast for Bread Making by Frozen Dough Method", Applied and Environmental Microbiology 52(4): 941-943 (Oct. 1986).
Panek "Trehalose Metabolism and Its Role in *S. cerevisioe*" Journal of Biotechnology 3(3): 121-130 (1985).
App et al. "Purification and Characterization of Neutral Trehalase from Yeast Abysl Mutant" Journal of Biological Chemistry 264(29): 17583-17588 (Oct. 1989).
*Patent Abstracts of Japan* (Dec. 7, 1989) vol. 13, No. 549, (C-622) [3897].
Boos et al., *J. Biol. Chem.* (1987) 262:13212-13218.
Thevelein *Microbiol. Rev.* (1984) 48(1): 42-59.
Pollock *Cereal Chem.* (1951) 28: 498-505.
Mackenzie et al., *J. Gen. Microbiol.* (1988) 134: 1661-1666.
Hottinger et al., *FEBS Lett.* (1987) 220(1):113-115.
Gadd et al., *FEMS Microbiol. Lett.* (1987) 48:249-254.
Simard et al., *Curr. Genet.* (1988) 14:461-470.
Morris et al., *J. Gen. Microbiol.* (1986) 132:2023-2034.
Tamanoi *Biochem. Biophys. Acta* (1988) 948:1-15.
Tatchell et al., *Proc. Natl. Acad. Sci.* (1985) 82: 3785-3789.
Toda et al, *Cell* (1985) 40: 27-36.
Uno et al., *J. Biol. Chem.* (1983) 258 (18):10867-10872.
Panek et al., *Curr. Genet.* (1987) 11: 459-465.
Vandercammen et al., *Eur. J. Biochem.* (1989) 182:613-620.
Harris et al., *Can. J. Microbiol.* (1988) 34:835-838.
Van der Plaat et al., *Biochem. Biophys. Res. Comm.* (1974) 56:580-587.

*Primary Examiner*—Richard A. Schwartz
*Assistant Examiner*—James Ketter
*Attorney, Agent, or Firm*—Morrison & Foerster

[57] ABSTRACT

A transformed yeast is disclosed, comprising at least one gene encoding neutral trehalase or trehalose-6-phosphate synthase which gene has been modified such that it differs from a corresponding wild-type gene encoding neutral trehalase or trehalose-6-phosphate synthase, the yeast having as a result a different trehalose content from the untransformed parent yeast. The sugar resistance and drying resistance of the yeast compared to those of the untransformed strain are thereby improved.

1 Claim, 1 Drawing Sheet

RECOMBINANT DNA ENCODING NEUTRAL TREHALASE

CROSS-REFERENCE TO RELATED APPLICATION

This is a continuation-in-part of U.S. application Ser. No. 07/577,888, filed Sep. 5, 1990, now abandoned, and claims priority thereto pursuant to 35 USC 120.

FIELD OF THE INVENTION

This invention relates to yeast, especially baker's yeast.

BACKGROUND OF THE INVENTION

It is well known that yeast strains belonging to the genus Saccharomyces are capable of fermenting sugars to approximately equal amounts of carbon dioxide and ethanol under anaerobic conditions. The leavening activity of yeast in dough is a result of this activity. The rate of carbon dioxide and ethanol evolution in dough is dependent upon, besides the activity of enzymes involved, the sensitivity of the yeast against the amount of sugar present in the dough. In sugar-rich doughs the leavening activity of the yeast may be much lower than in lean (nonsugared) doughs, caused by a higher osmotic pressure related to the presence of the sugar.

The commercial product baker's yeast is produced in several formulations comprising fresh yeast, dried yeast and frozen yeast. Fresh yeast is available as compressed yeast (27-33% dry matter content) and cream yeast (17-23% dry matter content). Dried yeast is available as active dry yeast (ADY) and as instant dry yeast (IDY) with moisture contents of 6-8% and 3-6%, respectively. Improving the fermentative power of yeast is an ongoing research effort. Both the dried yeast and the moist yeast may be improved to increase their carbon dioxide producing ability in lean (non-sugared) as well as in rich (sugared) doughs so as to reduce leavening time and/or enable the use of less yeast, a considerable cost factor in baking.

Role of trehalose in yeast cells

Trehalose (alpha-D-glucopyranosyl-alpha-D-glucopyranoside) is an important storage compound in vegetative cells and spores of fungi and yeasts. Trehalose appears to serve mainly as a storage carbohydrate during periods of non-proliferation. This applies to the life cycle, the cell cycle and other conditions under which cessation of growth occurs, such as (for example) starvation (Thevelein, J. M. (1984) Microbiol. Rev, 48, 42-59)

Trehalose is accumulated at the end of the reproductive stages and appears to be of importance for the viability of resting cells (Thevelein, ibid.). The high trehalose levels in fungal spores are also believed to enhance the resistance of the spores under extreme environmental conditions, such as high and low temperatures and desiccation. Besides a role for trehalose in the viability of spores, several investigators have found a relationship between the level of intracellular or extracellular content of trehalose and stress resistance: the trehalose level is positively correlated with the gassing power of dry yeast (Pollock, G. E., Holstrom, C. D. (1951) Cereal Chem. 28. 498-505). Also a positive correlation of the trehalose level with osmotolerance (Mackenzie, K. F., Sing, K. K., Brown, A. D. (1988), J. Gen. Microbiol. 134, 1661-1666) and with heat tolerance was found (Hottiger, T., Boller, T., Wiemken, A. (1987), FEBS Lett., 220. 113-115). In another study it was found that the level of exogenous, added trehalose correlated with dehydration resistance in stationary phase cells but not in exponential phase cells (Gadd, G. M., Chalmers, K., Reed, R. H. (1987), FEMS Microbiol. Lett., 48, 249-254).

Elevation of the cellular trehalose level.

There is a need to produce yeast of higher quality, such as yeast having higher gassing power. Such a yeast may be obtained by elevating the cellular trehalose content of the yeast. This decreases the harmful effects of several forms of stress on the yeast. Elevation of the cellular trehalose level occurs, under conditions that will lower the growth rate, which can e.g. be achieved by starvation, elevated temperatures and, in general, by forms of stress such as drying and freezing. In yeast manufacturing the lower growth rate can be achieved by lowering the molasses feed at the end of the fermentation. High trehalose levels can also be obtained by applying severe forms of stress as said before. However, these conditions result in yeast with altered properties and lower quality (e.g. viability, gassing power), due to side effects of the applied conditions (Jimenez J., Benitez T., (1988) Curr. Genet. 119, 541-547 and Morris G. J., Winters L., Contson G. E., Clarke K. J. (1983) J. Gen. Microbiol., 129, 2023-2034).

Genetic modification of the trehalose level has been achieved using yeast strains mutated in the RAS2 gene. Yeast RAS proteins are guanine nucleotide-binding proteins and are involved in cAMP formation and possibly also in turnover of inositol phospholipids. Both RAS1 and RAS2 proteins exhibit activities to bind guanine nucleotides as well as to hydrolyze GTP, while this latter activity is abolished in $RAS^{val19}$ mutants, in which the nineteenth amino acid (glycine) is changed into valine.

The $RAS^{val19}$ mutants exhibit multiple dominant phenotypes which include: (1) failure to accumulate storage carbohydrates such as glycogen and trehalose; (2) inefficient sporulation; (3) sensitivity to nutrient starvation; and (4) sensitivity to heat-shock treatment. Strains which lack the RAS2 gene exhibit virtually opposite phenotypes which include: (1) accumulation of storage carbohydrates and (2) sporulation even on rich media. These mutants fail to grow efficiently on nonfermentable carbon sources and cells homozygous for RAS2 disruptions sporulate on rich media (Tatchell, K., supra). These phenotypes are similar to the phenotypes of yeasts affected in the cAMP pathway (Tamanoi, F. (1988) Biochim. Biophys. Acta., 948, 1-15).

There are conflicting data published concerning the relation between trehalose levels and trehalase activity in the cell.

Specifically, mutations in the RAS2 gene resulted in low levels of neutral trehalase, the trehalose mobilizing enzyme, and elevated levels of accumulated trehalose in early stationary phase cells in the case of a ras2− mutation (Tatchell, K., Robinson, L. C., Breitenbach, M. (1985), Proc. Natl. Acad. Sci., 82, 3785-3789). High levels of neutral trehalase and no accumulation of trehalose in stationary phase yeast cells occur with a $RAS2^{val19}$ mutation (Toda, T., Uno, I., Ishikawa, T., Powers, S. Kataoka, T., Broek, D., Cameron, S., Broach., J., Matsumoto, K., Wigler, M. (1985), Cell, 40, 27-36).

Resistance against different forms of stress was not tested in the mutants mentioned above.

In yet another study, mutants with defects in the cAMP dependent protein kinase cascade were used. A bcyl mutation (cAMP independent protein kinase) resulted in a high level of neutral trehalase and low levels of trehalose, while a cyrl-2(ts) mutation (thermolabile adenylate cyclase and low levels of cAMP) resulted in a low level of neutral trehalase and a normal level of trehalose, opposite to the results obtained with the ras2 mutants. (Uno, I., Matsumoto, K., Adachi, K., Ishikawa, T. (1983) J. Biol. Chem., 258, 10867–10872).

Like the physiologically or environmentally induced modifications of the trehalose content of yeast, such as growth at higher temperatures or starvation conditions, the above mentioned genetically induced modifications have negative side-effects besides elevation of the trehalose content. Therefore modification of the trehalose content genetically via said mutations is not useful for industrial application.

Opposite results about the existence of a direct relationship between the neutral trehalase level and trehalose level in yeast have been presented by different research groups e.g. compare ras2 mutants, which have a lower neutral trehalase and higher trehalose content, with cyrl-2(ts) mutants, which have a lower neutral trehalase but no higher trehalose content.

Regulation of the trehalose metabolism in yeast

Trehalose is synthesized from glucose-6-phosphate and UDP-glucose, catalyzed by trehalose-6-phosphate synthase, to form trehalose-6-phosphate, which is processed to trehalose by trehalose-6-phosphate phosphatase. Panek and coworkers (Panek A. C., De Araujo P. S., Moura-Neto V. and Panek A. D. (1987) Curr. Genet., 11, 459–465) claim that trehalose-6-phosphate synthase activity is inactivated by the cAMP dependent protein kinase. Others, however, claim that trehalose-6-phosphate synthase is not affected by cAMP dependent protein kinase (Vandercammen A., Francois J. and Hers H. (1989) Eur. J. Biochem., 182, 613–620). Trehalose-6-phosphate synthase activity was measured in stationary phase cells and appeared to be independent of ATP, cAMP and cAMP dependent protein kinase.

Trehalose breakdown is performed by a neutral, cytoplasmic trehalase, which activation is mediated by phosphorylation by the cAMP dependent protein kinase. The non-phosphorylated form is inactive (Uno, I., Matsumoko, K., Adachi, K., Ishikawa, T. (1983), J. Biol. Chem., 258, 10867–10872). In addition the vacuole contains a so-called acid trehalase which function is not yet known (Harris S. D., Cotter D. A. (1988) Can. J. Microbiol. 34, 835–838).

After a glucose pulse a substantial increase in the intracellular concentration of cyclic-AMP is observed in the first few minutes during the lag phase preceding growth. This is followed by a 6-8 fold increase in the neutral trehalase activity concomitant with the rapid degradation of trehalose. After approximately one hour the neutral trehalase activity is decreased to the low level of activity measured before activation. (Van der Plaat, J. B., Van Solingen, P. (1974) Biochem. Biophys. Res. Comm., 56, 580–587).

Whereas reduced growth is associated with trehalose accumulation, the induction of growth in resting stages is associated with the rapid mobilization of trehalose due to the activation of trehalase. Addition of a nitrogen source enhances trehalose breakdown and prevents resynthesis (cf. Thevelein (1984) Microbiol. Rev., 48. 42–59).

The literature data strongly suggest that during periods in which trehalose synthesis is necessary only trehalose-6-phosphate synthase is active while neutral trehalase is inactive and therefore it is prevented that trehalose synthesis and breakdown occur at the same time.

SUMMARY OF THE INVENTION

The present invention provides a transformed yeast comprising at least one gene encoding neutral trehalase or trehalose-6-phosphate synthase which gene has been modified such that it differs from a corresponding wild-type gene encoding neutral trehalase or trehalose-6-phosphate synthase, the yeast having as a result a different trehalose content from the untransformed parent yeast. The transformed yeast of the invention has improved stress resistance compared to the untransformed yeast strain, without the occurrence of the previously mentioned negative side-effects. Furthermore the invention provides an efficient method of trehalose production.

DETAILED DESCRIPTION

By 'stress resistance' is meant throughout the present application a higher tolerance to stress conditions e.g. higher osmotic pressure, elevated temperature or conditions of desiccation.

By 'fermentation yield' is meant grams of dry biomass formed per gram of sugars consumed.

By 'neutral trehalase' is meant the cytoplasmic trehalase responsible for the trehalose breakdown.

By 'stringent hybridization' is meant hybridization conditions as described in Maniatis et. al. (T. Maniatis, E. E. Fritsch, J. Sambrook (1982), Molecular Cloning, A Laboratory Manual), pp. 387–389.

These condition are as follows:

The hybridization solution is 6x SSC, 0.01M EDTA, $^{32}$p-labeled denatured probe DNA, 5x Denhardt's solution, 0.5% SDS and 100 μg/ml denatured salmon sperm DNA. The hybridization conditions typical for this procedure are given in the following table:

| DNA on filter | Sp. act. of Probe DNA (cpm/μg) | Amount of probe added | Time of hybridization (hr) |
|---|---|---|---|
| Fragments of cloned DNA (~100 ng/ fragment) | $10^7$ | $10^5$–$10^6$ cpm (0.01–0.1 μg) | 3–4 |
| Total eukaryotic DNA (10 μg) | $10^8$ | $1 \times 10^7$ cpm –$5 \times 10^7$ (0.1–0.5 μg) | 12–16 |

The hybridization is conducted at 68° C. for the required time of hybridization.

The filters are washed in 2x SSC and 0.5% SDS at room temperature for 5 minutes, then with 2x SSC and 0.1% SDS for 15 minutes at room temperature with gentle agitation, and then at 0.1X SSC and 0.5% SDS at 68° for 2 hours with gentle agitation, and then with 0.1x SSC and 0.5% SDS at 68° for 30 minutes.

Surprisingly it has been found now that both neutral trehalase and trehalose-6-phosphate synthase are active when, during the production of baker's yeast, trehalose is synthesized. This is unexpected because during trehalose synthesis, the neutral trehalase is supposed not to be active. This discovery is applied to increase the trehalose content of yeast by modifying the cellular level of trehalase.

According to one aspect of the present invention, the neutral trehalase activity in the yeast cell is lowered by the manipulation of the neutral trehalase gene, thereby increasing the intracellular trehalose content. The thus obtained yeast will have a higher stress resistance.

This approach has the advantage that side effects that have so far occurred simultaneously with trehalose elevation as a result of other genetic or physiological modifications, do not occur in the yeast with a modified cellular neutral trehalase content. Therefore a yeast with an elevated trehalose level due to a modified trehalase content is suitable for industrial use.

According to the invention, yeast strains are provided with improved properties under production and application conditions. With improved properties as used in the specification in connection with the present (modified) yeast strains, is meant higher baking performance, especially improved drying resistance relative to the corresponding untransformed (wild-type) strain and/or higher sugar resistance relative to the corresponding untransformed (wild-type) strain.

Therefore methods are provided for the construction of yeast strains having a higher trehalose content compared to the parent strain. These methods encompass the use of genes which code for enzymes involved in trehalose metabolism, such as trehalose-6-phosphate synthase, trehalose-6-phosphate phosphatase and trehalase. In this way it is possible to regulate the trehalose content of the cell without interference with other metabolic processes (such as described before).

In a preferred embodiment of the invention the gene encoding the neutral trehalase has been isolated. The availability of this gene enables the decrease of the trehalase activity in the cell via the well-known technique of gene-disruption (Rothstein R. J. (1983) in 'Methods in Enzymology' 101, 202) of the respective gene(s). For instance, in a diploid yeast strain one or even both alleles of the trehalase gene can be inactivated (assuming that in a haploid genome, one copy of the trehalase gene is present).

In another embodiment of the invention the neutral trehalase gene can be modified such that a phosphorylation site of the trehalase is modified and phosphorylation cannot occur anymore. It is known from literature that neutral trehalase is activated through phosphorylation, which activation is catalyzed by a cAMP dependent protein kinase. Non-phosphorylated trehalase has a much lower activity. The cyclic AMP-dependent protein kinase consensus recognition site can be modified such that phosphorylation cannot take place anymore. This generates a gene encoding an altered neutral trehalase which cannot be activated anymore via phosphorylation. Any residual activity of the non-phosphorylated trehalase may well be important for the physiology of the cell. This alternative approach therefore may well be the approach of choice in the case that some mobilization of trehalose during biomass formation or in the initial period of baker's yeast performance in dough is essential.

In another embodiment of the invention the gene encoding neutral trehalase is mutagenized at random. Genes coding for trehalase with a lower activity are isolated and used for gene-replacements of the unmodified gene(s) of a yeast strain. Also this approach will lead to an overall lower activity of trehalase and hence a higher level of trehalose.

In another embodiment of the invention the gene encoding neutral trehalase is brought under control of an inducible promoter thereby permitting controlled expression of this gene. This will make it possible to render the gene active under conditions where trehalase activity is beneficial for the cell and to shut off its gene expression under conditions where a stable high trehalose level is wanted, for instance at the end of the yeast biomass production stage.

In another embodiment of the invention the gene coding for neutral trehalase is brought under control of a promoter which is weaker than the promoter of this particular gene.

In still another embodiment of the invention the expression of the neutral trehalase gene(s) can be regulated via the anti-sense RNA approach. In this case, anti-sense RNA of (parts of) the neutral trehalase gene is made in the cell by cloning the coding region (or parts of) in opposite orientation behind a promoter. The RNA synthesized from this gene can base-pair with normal neutral trehalase RNA, thereby preventing its translation. The efficiency with which double stranded RNA is formed ultimately determines the level of neutral trehalase synthesis. Therefore this approach is an alternative to regulate gene expression and is of interest in case the genome contains a family of trehalase genes. Since antisense RNA acts in trans such a family of genes can be regulated in a simple way.

In another embodiment of the invention the gene encoding vacuolar acid trehalase is isolated. With this gene as tool this type of trehalase activity can be modified, for instance via gene-disruption techniques, protein engineering, or exchange of promoters (inducible, weaker). This approach is of value when in the absence of any neutral trehalase activity still substantial mobilization of trehalose occurs via the acid trehalase. Therefore, this approach can be used to obtain an optimal level of trehalose in the cell.

In still another embodiment genes encoding enzymes which are directly involved in the synthesis of trehalose, such as trehalose-6-phosphate synthase and trehalose-6-phosphate phosphatase, are cloned. Enhancing the rate of trehalose biosynthesis is another direct approach to increase the level of trehalose. Such an increase can be obtained via genetic engineering techniques applied onto these trehalose biosynthetic genes (increase of gene copy number, protein engineering in order to alter specific activities, use of other promoters and the like).

All these abovementioned embodiments have in common the use of genes coding for enzymes which are directly involved in trehalose metabolism to enhance the trehalose level in the cell. Such an enhanced level is of advantage under conditions of stress, like heat, osmotic pressure, desiccation, frozen dough, and the like.

The yeasts obtained with the above mentioned techniques can be used in strain improvement programs using techniques like DNA mediated transformation techniques as well as techniques like protoplast fusion, mass mating or mutation. Also combinations of these techniques are possible. For example, transformed yeasts can be crossed with another (production) strain. The yeast strains obtained with such improvement programs are included in the scope of the invention.

According to the invention a yeast strain belonging to the genes Saccharomyces or to the genus Kluyveromyces is used, advantageously a strain belonging to S. cerevisiae is applied.

The present invention also provides methods of making doughs (normal and frozen dough), bread and similar products using the yeast of the invention to generate carbon dioxide.

The present invention also provides a yeast with a high content of intracellular trehalose thereby permitting an efficient way of trehalose production.

Cloning techniques

For general cloning techniques reference is made to the handbook of Maniatis et al. (T. Maniatis, E. F. Fritsch, J. Sambrook (1982) Molecular Cloning, A Laboratory Manual). Restriction enzymes are used as recommended by the manufacturer and are obtained either from New England Biolabs (Biolabs), Bethesda Research Laboratories (BRL) or Boehringer Mannheim (Boehringer). In general 1 to 5 units of enzyme are needed to cleave 1 μg of DNA.

Transformation of E. coli was carried out using the $CaCl_2$-technique (T. Maniatis et. al., supra).

In further aspects the invention provides a recombinant plasmid or vector which comprises at least part of a neutral trehalase gene and wherein the neutral trehalase gene has been optionally modified in such a way that the said gene codes for trehalase with an activity which is lower than that of the corresponding wild-type gene. It also provides a recombinant plasmid or vector which comprises at least part of a trehalose-6-phosphate synthase gene and wherein the trehalose-6-phosphate synthase gene has been optionally modified in such a way that the said gene codes for trehalose-6-phosphate synthase with an activity which is greater than that of the corresponding wild-type gene.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity and understanding, it will be readily apparent to those of ordinary skill in the art in light of the teachings of this invention that certain changes and modifications may be made thereto without departing from the spirit and scope of the appended claims.

The following experimental data are given to illustrate the invention. It has to be understood that a person skilled in the art who is familiar with the methods may use other yeast strains and vectors which can be equally used for the purpose of the present invention. These alterations are included in the scope of the invention.

Lists of deposits (clone, strains and hybridoma cell line)

The following phage clone, strains or cell line have been deposited with CBS (Centraalbureau Voor Schimmelcultures Oosterstraat 1, 3742 SA Baarn, the Netherlands, and with ECACC (European Collection of Animal Cell Cultures (ECACC), PHLS-Center for Applied Microbiology and Re-search, Porton Down, Salisbury, Wiltshire SP4, OJG, UK).

| lambda st 11 clone | Accession number | deposition date |
|---|---|---|
| lambda TRE 16.1.1 | CBS 512.90 | November 22, 1990 |
| Strains | Accession number | deposition date |
| Saccharomyces cerevisiae GRD 11-21 (strain G) | CBS 154.91 | March 5, 1991 |
| Saccharomyces cerevisiae | CBS 155.91 | March 5, 1991 |

-continued

| | | |
|---|---|---|
| 227 Ng Saccharomyces cerevisiae 237 Ng (strain A) | CBS 158.86 | March 25, 1986 |
| Escherichia coli harbouring plasmid pTRE16.1.1 | CBS 115.91 | February 19, 1991 |
| Escherichia coli harbouring plasmid pTZ19R | CBS 405.87 | September 3, 1987 |
| Hybridoma cell line producing monoclonal antibody 41-2F10 | ECACC 90121901 | December 14, 1990 |

Figure 1:
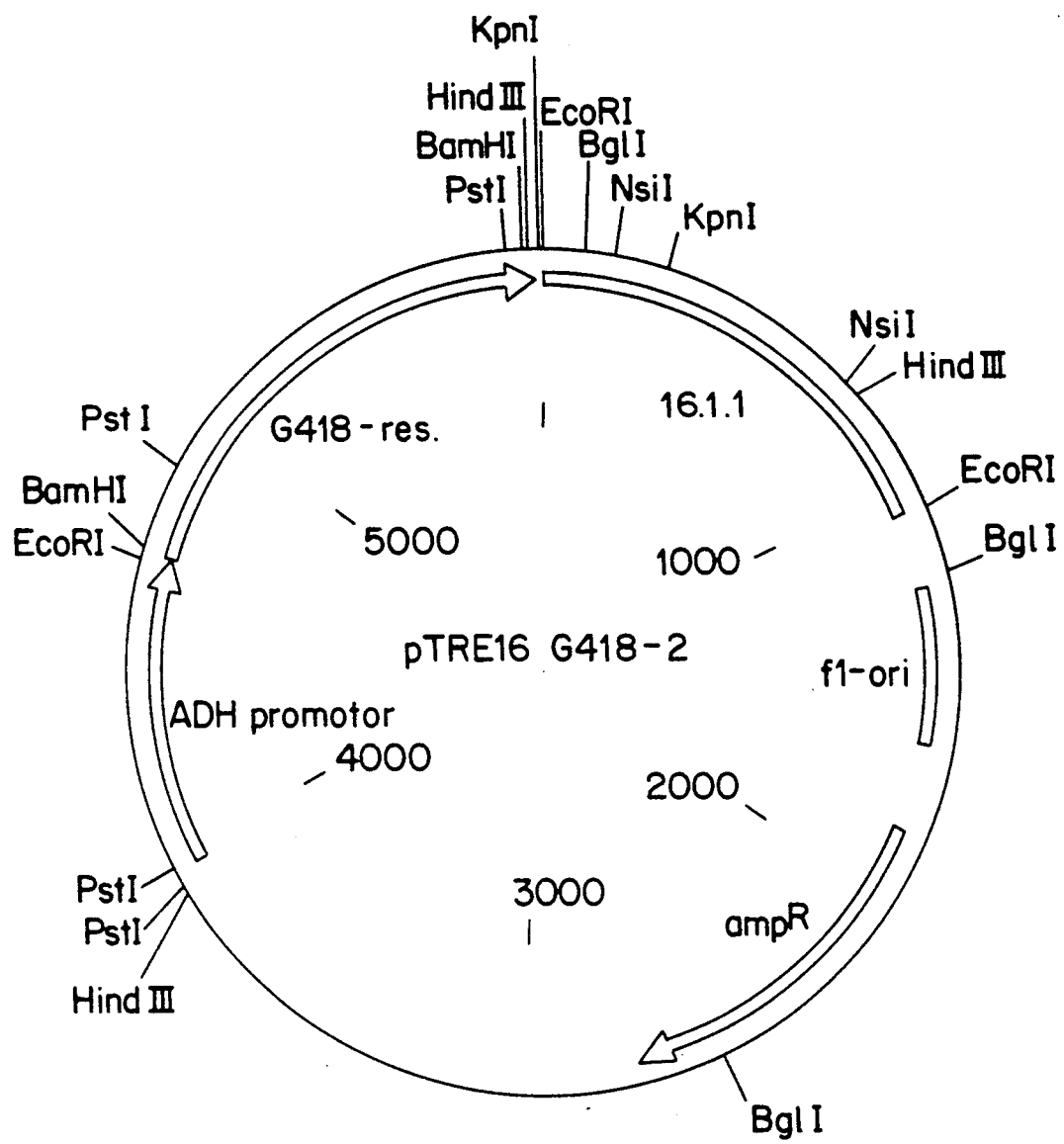
FIG. 1 gives the structure of plasmid pTRE16G418-2. Arrows indicate the direction of transcription. The orientation of the 16.1.1 segment is not known yet.

Abbreviations: G418-res, Tn5 gene, conferring resistance to G418; ADH promoter, Saccharomyces cerevisiae promoter of ADHI gene, linked to G418-res; f1 ori, origin of replication of phage f1; ampR, ampicillin resistance gene; 16.1.1, yeast insert as also present in lambda TRE 16.1.1, containing part of the neutral trehalase gene; furthermore, relevant restriction sites have been indicated. The two EcoRI sites at the borders of the 16.1.1 segment are not necessarily present at the corresponding position in the genome of Saccharomyces cerevisiae. At least one of these sites results from the way the lambda gt 11 cDNA bank has been constructed. In the innercircle, length is indicated in base pairs.

EXAMPLE 1

ACTIVITY OF TREHALASE AND TREHALOSE CONTENTS OF BAKER'S YEAST

Aerobic (fed-batch) fermentation

A yeast cream was prepared using a Saccharomyces cerevisiae yeast strain 227 Ng.

A lyophilized culture sample was cultivated in the usual way up to the desired amount of seed yeast. For the cultivation of yeast, laboratory fermentors were used with a content of 10 liters (net volume - 6 liters), provided with a device for a continuous supply of molasses and of an assimilable nitrogen source. The fermentors were also provided with a device for the regulation of the pH and for temperature control. The fermentations were carried out essentially according to G. Reed and H. J. Peppler, Yeast Technology, The AVI Publishing Company Inc., Westport Conn., U.S.A., 1973. The cultivation conditions were in particular:

Molasses mixture, consisting of 80% by weight of beet molasses and 20% by weight of cane molasses, calculated on the basis of 50% sugar;

Molasses supply (according to Reed and Peppler, page 78/79) according to Table 1;

The required amount of phosphate was added in the form of mono-ammoniumphosphate, prior to inoculation;

The required amount of nitrogen was supplied as a 10% solution of $NH_3$ in water, according to Table 1, below;

The temperature was kept at 30° C. during the whole fermentation period;

pH (Reed and Peppler, page 67/68) was kept at 5.0 during the whole fermentation period);

vitamin $B_1$ was added in an amount of 6 mg/kg of molasses ad 50% sugar at the initial stage of the fermentation.

The yeast obtained by these fermentations was concentrated and washed with tap water in a laboratory nozzle centrifuge.

TABLE 1

| Time hours | g. Molasses ad 50% sugar (in total) | g. ammonia ad 10% (in total) |
| --- | --- | --- |
| 0.00 | 49 | 20 |
| 1.00 | 49 | 20 |
| 2.00 | 49 | 20 |
| 3.00 | 69 | 23 |
| 4.00 | 108 | 32 |
| 5.00 | 168 | 52 |
| 6.00 | 246 | 77 |
| 7.00 | 325 | 102 |
| 8.00 | 404 | 132 |
| 9.00 | 503 | 166 |
| 10.00 | 601 | 200 |
| 11.00 | 700 | 228 |
| 12.00 | 798 | 228 |
| 13.00 | 897 | 228 |
| 14.00 | 976 | 228 |

Enzyme levels were determined in samples taken during the desired feedbatching fermentations.

After filtration, pellets were resuspended in extraction buffer (MES, 25 mM; $CaCl_2$, 2.5 m,M; PMSF, 1 mM; ph=7). Cell extracts were made by adding ballotini beads (3 g/ml) and shaking in a vibrax VXR tube shaker 3 times for 3 minutes; cooling between shaking periods (0° C.). Extracts were centrifuged during 10 minutes at 12000×g and dialyzed overnight against buffer (MES, 5 mM; $CaCl_2$, 2.5 mM; pH=7).

Determination of trehalase activity in the cell free extracts was performed according to Thevelein, J. M., Van Laere, A. J. Beullens, M., Van Assche, J. A., Carlier, A. R. (1983) J. Gen. Microbiol., 129, 716–726, with the exception that tetramethylbenzidine was used as a glucose reagent instead of o-dianisidine. 1 U of trehalase activity is defined as 1 μmol glucose produced per minute.

Trehalose content of the cells was determined with HPLC as follows: fermentation samples were filtered, washed and subsequently boiled. After centrifugation to remove large cell fragments, the supernatant was diluted with acetonitril and water to a final concentration of acetonitril of 50% (v/v). The sample was filtered (0.45 μm) before they were applied to a carbohydrate column with RCSS precolumn and eluted with acetonitril/water, 4:1. Trehalose contents were determined with aid of a refractive index detector and an integrator.

Protein of cell free extracts was determined by the BCA method (Pierce). BSA served as a standard.

The neutral trehalase appeared to be constantly active during the fedbatch fermentation, even when trehalose accumulation starts at approximately 9 hours of fermentation (see Table 2). This result was unexpected because trehalase is supposed to be inactive during trehalose synthesis.

The idea of lowering the cell's neutral trehalase activity was based on this unexpected finding of trehalase being active throughout the fedbatch fermentation.

TABLE 2

| Hours | Trehalose % (w/w) | Trehalase (mU/g dry weight) |
| --- | --- | --- |
| 2 | 0.3 | 5.1 |
| 3 | 0.3 | 6.2 |
| 4 | — | 6.0 |
| 5 | 0.4 | 5.4 |
| 6 | 0.1 | 6.8 |
| 7 | 0.1 | 6.2 |
| 8 | 0.1 | 5.9 |
| 9 | 0.3 | 6.1 |
| 10 | 0.6 | 7.0 |
| 11 | 1.8 | 6.3 |
| 12 | 2.7 | 7.2 |
| 13 | 3.6 | 7.5 |
| 14 | 4.1 | 7.8 |
| 14.5 | 5.2 | 7.7 |
| 15 | 5.1 | 7.3 |

EXAMPLE 2

ISOLATION OF PHAGE LAMBDA CLONES CONTAINING PART OF THE GENE CODING FOR NEUTRAL TREHALASE

DNA encoding neutral trehalase was isolated by immuno screening of a lambda gt11 cDNA expression library. Use has been made of a monoclonal antibody (abbreviated 41-2F10) which is directed against the 80 kd subunit of neutral trehalase. This monoclonal has been deposited on Dec. 14, 1990 with the European Collection of Animal Cell Cultures (ECACC), PHLS-Center for Applied Microbiology and Re-search, Porton Down, Salisbury, Wiltshire SP4, OJG, UK, under the accession number 90121901. This monoclonal antibody reacts with one band of 80 kd on a Western blot prepared from an SDS-PAGE gel onto which a cell free extract of Saccharomyces cerevisiae was applied. Also, after incubation of the monoclonal antibody coupled to agarose beads (Afti-Bel Hz hydrazie, Bio-Rad Laboratories, Richmond, Calif., U.S.A.) with a cell free extract from Saccharomyces cerevisiae neutral trehalase activity is specifically bound to the gel material. After spinning down the beads less than 1% of the neutral trehalase activity is detectable in the supernatant.

The lambda gt11 yeast cDNA library was obtained from Clontech laboratories, Inc. 4030 Fabian way, Palo Alto, Calif. 94903 U.S.A. This library, catalog no. YL 1005b, lot no. 3411, was screened with the monoclonal antibody 41-2F10 according to procedures as described in the Protoblot® immunoscreening system of Promega (catalog no. S3710). See for the screening procedures also Huynh T. V., Yound R. A. and Davis R. W. (1985) in: DNA cloning, A practical approach, vol. 1 (D. M. Glover, ed.), pp. 49–78, IRL Press, Oxford.

Several positively reacting clones have been isolated. Lambda TRE16.1.1 has been analyzed further (see below). This phage clone has been deposited with the Centraalbureau voor Schimmelcultures (CBS), Oosterstraat 1, 3742 SA Baarn, the Netherlands on Nov. 22, 1990 under the accession number CBS 512.90.

An appropriate procedure to propagate the deposited phage clone has been described in Huynh T. V. et. al. (see above). E. coli strain Y1090 (ATCC no. 37197) has been used as host for propagation of the phage clone (see also Hutghn T. V., ibid.).

EXAMPLE 3

CONSTRUCTION OF RECOMBINANT PLASMIDS (a) pTRE16.1.1.

The yeast insert of lambda TRE16.1.1, has been clones into the commercially available vector pTZ19R (Pharmacia). This vector has been deposited at the Centraalbureau voor Schimmelcultures, Baarn, The Netherlands, under the accession number 405.87. The cloning procedure was as follows:

Firstly the yeast insert has been amplified. This was done essentially as described in "PCR Protocols, a guide to methods and applications (Eds. M. A. Innis, D. H. Gelfand, J. J. Sninsky and T. J. White 1990), pp. 253–258", with the following modifications: plaques have been used rather than a phage suspension; the 10×Taq polymerase buffer contains 20 mM $MgCl_2$; the thermal cycling was: 94° C. for 2 minutes, 55° C. for 2 minutes, 72° C. for 3 minutes. The oligonucleotide primers used in this reaction are complementary to DNA sequences surrounding the EcoRI cloning site of the lambda gt11 vector. Their sequences are 5'-GGCGAC-GACTCCTGGAGCCCG-3'(SEQ ID NO:1) and 5'-CACCAGACCAACTGGTAATGG-3+(SEQ ID NO:2). After the incubation, the reaction mixture was passed through a BIO-RAD RDP mini column in order to clean the DNA (removal of nucleotides).

Secondly, the PCR product was digested with EcoRI and cloned into pTZ19R×EcoRI to create plasmid pTRE16.1.1. This clone has been deposited at the CBS under the accession number 115.91 (on Feb. 19, 1991).

(c) Construction of pTRE16G418-2

In order to provide pTRE16.1.1 with a dominant selection marker, the following ligation has been carried out. A 1.9 kb BglII fragment containing the G418$^{res}$ gene under control of the ADHI promoter, was isolated after digestion of plasmid pRBN3 with BglII. pRBN3 has been described fully in European patent application EP-A-306107. This 1.9 kb BglII fragment was cloned into the BamHI site of pTRE16.1.1. This yielded pTRE16G418-2 (see FIG. 1).

EXAMPLE 4

CONSTRUCTION OF YEAST STRAINS WITH A DISRUPTED NEUTRAL TREHALASE GENE RESULTING IN LOWER NEUTRAL TREHALASE ACTIVITY

The yeast insert in pTRE16.1.1, when present in an expression vector, directs the synthesis of a polypeptide which is immunologically active against a monoclonal antibody raised against neutral trehalase. The insert gas a size of about 1100 bp and originates from a cDNA bank (see Examples 2 and 3). It has been characterized with some restriction enzymes as shown in FIG. 1. At this stage it was not know yet from which part of the gene this insert originated. Considering the estimated molecular weight of the neutral trehalase protein on a denaturing gel (about 80 kd (H. App and H. Hlozer, J. Biol. Chem. 264, 17853, 1989), the 1100 bp yeast insert most likely does not contain the whole gene.

According to one embodiment of the invention a yeast strain is provided with a diminished neutral trehalase activity. One way to get such a yeast is to disrupt the gene encoding neutral trehalase. In general, having cloned a gene or part of a gene, there are several methods to disrupt that particular gene in the genome (see Methods in Enzymology, vol. 185, chapter 23: Manipulating yeast genome using plasmid vectors, by T. Stearns, H. Ma and D. Botsten, 1990, Academic Press).

In one approach, the plasmid-borne copy of the gene (i.e. neutral trehalase) is truncated in such a way that it lacks both ends (the true amino terminal and carboxyl terminal regions are missing). Integration of this construct into the chromosome at the neutral trehalase locus leads to two nonfunctional copies of the gene, one lacking its 5' end, the other its 3' end. This approach has also been followed by us. We reasoned that the 1100 bp insert most likely does not contain the true 5' and 3' end, but only gene-internal sequences. Therefore, we made plasmid pTRE16G418-2, and digested that with NsiI. NsiI cuts twice in plasmic pTRE16G418-2, both times in the part of the neutral trehalase gene (see FIG. 1). This digestion generates recombinogenic ends and will direct the integration to the corresponding locus in the genome.

The analysis of the transformants obtained is fully described further below, but at this stage it is already mentioned that the transformants indeed have a diminished neutral trehalase activity. This proves that 1) the yeast insert is part of the neutral trehalase gene and
2) that indeed the yeast insert as present in pTRE16.1.1 (and in pTRE6G418-2) lacks both ends of the neutral trehalase and that is contains a gene-internal segment. In this context we note that we have isolated this yeast insert from a cDNA bank. Almost all the known genes in *Saccharomyces cerevisiae* do not contain introns, and hence we assume that also the neutral trehalase gene is not split. In that case the isolated cDNA clone is colinear with the corresponding genomic gene segment. In case the neutral trehalase gene appears to have introns then still the approach we have followed to disrupt the trehalase gene, will work.

The transformation procedure itself has been carried out as described in European patent application EP-A-306107. Two *Saccharomyces cerevisiae* strains have been used as host: *Saccharomyces cerevisiae* 237 Ng (deposited with the CBS under the accession number 158.86) and *Saccharomyces cerevisiae* GRD 11-21, a diploid strain (deposited with the CBS under the accession number 154.91). For selection of transformants use has been made of the aminoglycoside G418.

These two *Saccharomyces cerevisiae* strains have been transformed with pTRE16G418-2×NsiI. From each transformation, one transformant has been analyzed in further detail. The transformant of strain 237 Ng is abbreviated as ApTRE-dis, the transformant of strain GRD11-21 is abbreviated as GpTRE-dis.

Southern-blot analyzes of the genomic DNA of these transformants have confirmed that integration indeed took place at the resident neutral trehalase gene. In both transformants, one allele has been disrupted this way. We note that in the transformants also at least one allele is still unaltered, since both parents are at least diploid (not shown).

Several experiments support the conclusion that indeed the neutral trehalase gene has been disrupted in the transformants (see also Example 5). In one set of experiments, the neutral trehalase activities of parent strain A and its transformant ApTRE-dis has been measured. This was done as follows. Yeasts were grown overnight in shake flasks either in YEP-2.5% glucose or in YEP-2.5% glycerol, 0.2% glucose. Neutral trehalase activity was determined as described in Example 1. The measured activities have been summarized in Table 3. It can be concluded that neutral trehalase activity is significantly lowered in ApTRE-dis, which contains a disrupted neutral trehalase gene. We conclude that the yeast insert, which we have isolated in clone lambda TRE16.1.1 contains part of the gene encoding neutral trehalase.

TABLE 3

Neutral trehalase activity in strain A and its transformant ApTRE-dis (mU/mg cell free extract protein)

| Strain | C-source | |
|---|---|---|
| | Glucose | Glycerol + Glucose |
| A | 26.1 | 27.7 |
| ApTRE-dis | 12.2 | 14.7 |

The above mentioned example illustrates one possibility to alter the level of neutral trehalase. Alternative methods are possible as well. Some possibilities are described below.

The yeast insert of the isolated phage clone is suitable to perform gene disruption experiments. This can be carried out as follows: somewhat into such a yeast sequence a DNA segment can be cloned containing a gene that can function as selection market during in yeast transformation. Examples are the Ura3 gene (in case the recipient host yeast strain has a Ura3− auxotrophy) and so-called dominant selection markers. The latter confer resistance to antibotics such as gentamycin, hydgromycin B and phleomycin or to herbicides such as sulfometruon methyl. Examples are the G418 gene, conferring resistance to gentamycin and brought under control of a S. cerevisiae promoter (see for example EP 0306107) and the SMR1-410 gene of S. cerevisiae, conferring resistance to sulfometruon methyl (see Casey G., Xiao W. and Rank G. H., J. Inst. Brew. 1988, 94, 93-97). In this way, plasmids can be constructed containing a disrupted trehalase gene, interrupted by selection marker DNA (see above). Such a cassette can then be liberated from the vector backbone and used in gene-transpacement experiments, well described for yeast (Rothstein R. J., supra). In this way, a trehalase gene can be destroyed, resulting in a lower trehalase activity and hence in a higher trehalose content. It will be appreciated to recognize that in the case the host strain contains several trehalase genes, the procedure of gene transplacement can be repeated several times (for instance by using different selection markers). Such altered genes can be integrated into the genome of yeast using the gene-transplacement technique.

With the yeast insert 16.1.1 as probe a genomic library of *Saccharomyces cerevisiae* can be screened. This will ultimately result in the isolation of clones containing the entire neutral trehalase gene and its flanking sequences (promoter/terminator regions). Then, using standard procedures, the natural trehalase promoter can be substituted with a different promoter, preferably a homologous promoter. Such altered genes can be integrated into the genome using gene replacement techniques (Rothstein R. J., supra). This will allow to change the expression of the neutral trehalase gene such that ultimately a lower level of trehalase is being made.

Using standard procedures, the gene can be mutagenized such that it codes for an altered neutral trehalase which cannot be phosphorylated anymore.

It will be understood that the above listed methods are by no way exhaustive.

EXAMPLE 5

LEVELS OF TREHALASE ACTIVITY IN STRAINS A AND ApTRE-dis, AS DETERMINED IN CONTINUOUS CULTURE Since neutral trehalase activity is likely to be regulated by the growth rate of the cells, the effect of disruption of the neutral trehalase gene was determined at two different growth rates. To compare parent and disruption-mutant under identical conditions neutral trehalase activity was measured in cells growing in steady state, in a continuous culture.

Strain A and strain ApTRE-dis were grown in batch for 24 hours in Applikon fermentors (Applikon Dependable Instruments, Schiedam, The Netherlands) with a working volume of 2 liters. Medium and culture conditions were essentially as described by E. Postma, W. A Scheffers, J. P. van Diken (1989), Yeast 5, 159-165.

After starting the feed at a dilution rate of 0.06 $h^{-1}$ the culture reached steady state in 65 hours, and remained at steady state during 1 day. During that day samples were taken. Then feed was increased to a dilution rate of 0.15 $h^{-1}$. 48 hours later a steady state was reached, and samples were taken.

Activity of neutral trehalase is clearly dependent on the growth rate, as can be seen in Table 4. Both parent and disruption mutant showed higher activities at $D=0.06$ $h^{-1}$. At both dilution rates the activity of neutral trehalase of the disruption mutant was above half of the activity of the parent strain. This shows that independent of the growth rate the decrease in activity of neutral trehalase is roughly equivalent with the gene copy number.

TABLE 4

| | Trehalase activity (U/g dry weight) | |
|---|---|---|
| D ($h^{-1}$) | A | ApTRE-dis |
| 0.06 | 11.6 | 4.8 |
| 0.15 | 7.9 | 3.3 |

EXAMPLE 6

TREHALOSE CONTENTS OF TREHALASE-DISRUPTION MUTANTS OF BAKER'S YEAST

To determine the effect of disruption of a copy of the gene encoding neutral trehalase on the trehalose contents of the cells in the stationary phase the following experiment was performed:

Strains A, G, ApTRE-dis and GpTRE-dis were grown in duplo overnight in 500 ml shake-flasks containing 100 ml YEP-medium with 5% glucose. Cells were harvested in the stationary phase, collected and resuspended at t=0 min. in 70 ml of fresh YEP-medium containing 0.5% glucose. Samples were taken every 90 min. up to 7½ hours.

Trehalose content of the cells were determined with HPLC as follows: fermentation samples were filtered, washed and subsequently boiled. After centrifugation to remove large cell fragments that supernatant was injected directly on a Bio-Rad Aminex HJPX 87-H column. The column temperature as 65° C., and elution was performed with 0.01 N $H_2SO_4$. Trehalose content was determined with the aid of a refractive index detector and an integrator.

Cell free extracts were prepared as described in Example 1, with the exception that the cell free extracts were not dialyzed. Trehalase levels in the cell free extracts were determined as described in Example 1.

Table 5 shows at all time points clear differences between the levels of trehalose in parent and disrupted strains. Strain A initially has a higher trehalose content, which is under the conditions of the experiment less stable than the initially lower trehalose level of strain G.

The activity of neutral trehalase in strain G was clearly lower as compared with the activity in strain A (Table 5). Furthermore, in both strain ApTRE-dis and stain GpTRE-dis the trehalase levels were lower with respect to the parent strains (Table 5).

So by lowering the neutral trehalase activity by disruption of the structural gene encoding neutral trehalase it is possible to obtain a yeast with a higher trehalose content. This yeast appeared to be very useful for industrial application.

TABLE 5

| Hrs | Trehalose (%, w/w) | | | | Trehalase (U/g dry weight) | | | |
| --- | --- | --- | --- | --- | --- | --- | --- | --- |
| | A | ApTRE-dis | G | GpTRE-dis | A | ApTRE-dis | G | GpTRE-dis |
| 0 | 5.7 | 7.9 | 2.6 | 3.5 | 4.4 | 3.0 | 1.3 | 0.2 |
| 1½ | 3.7 | 6.0 | 2.7 | 3.6 | 5.5 | 3.2 | 1.3 | 0.9 |
| 3 | 2.1 | 5.3 | 2.7 | 3.3 | 3.9 | 3.8 | 1.5 | 1.4 |
| 4½ | 1.2 | 3.1 | 2.6 | 3.5 | 5.3 | 4.8 | 2.1 | 1.6 |
| 6 | 0.6 | 2.8 | 3.1 | 4.0 | 5.0 | 5.0 | 2.0 | 1.6 |
| 7½ | 0.1 | 2.5 | 3.2 | 4.3 | 5.4 | 4.6 | 2.7 | 2.0 |

Data are mean values of the duplo experiments

---

We claim:

1. A recombinant DNA comprising a gene or part of a gene coding for neutral trehalase of yeast selected from the group consisting of
   i) the NDA insert 16.1.1 in plasmid pTRE16.1.1 (CBS 115.91),
   ii) A DNA capable of hybridizing under stringent conditions to a DNA of i) and encoding a protein having the enzymatic activity of the protein encoded by i) and
   iii) A DNA encoding the same amino acid sequence as that of i) or ii).

* * * * *

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
( A ) LENGTH: 21 base pairs
( B ) TYPE: nucleic acid
( C ) STRANDEDNESS: single
( D ) TOPOLOGY: linear ( x i ) SEQUENCE DESCRIPTION: SEQ ID NO:1:

GGCGACGACT CCTGGAGCCC G    21

( 2 ) INFORMATION FOR SEQ ID NO:2:

( i ) SEQUENCE CHARACTERISTICS:
( A ) LENGTH: 21 base pairs
( B ) TYPE: nucleic acid
( C ) STRANDEDNESS: single
( D ) TOPOLOGY: linear ( x i ) SEQUENCE DESCRIPTION: SEQ ID NO:2:

CACCAGACCA ACTGGTAATG G    21